US006265383B1

(12) United States Patent
Haupert, Jr.

(10) Patent No.: US 6,265,383 B1
(45) Date of Patent: Jul. 24, 2001

(54) TREATMENT OF ISCHEMIC CARDIAC MALFUNCTION

(75) Inventor: Garner T. Haupert, Jr., Littleton, MA (US)

(73) Assignee: The General Hospital Corporation, Charlestown, MA (US)

( * ) Notice: Subject to any disclaimer, the term of this patent is extended or adjusted under 35 U.S.C. 154(b) by 0 days.

(21) Appl. No.: 09/326,953

(22) Filed: Jun. 7, 1999

Related U.S. Application Data

(62) Division of application No. 08/866,712, filed on May 30, 1997, now Pat. No. 5,910,484.

(51) Int. Cl.[7] ................................................ A61K 31/70

(52) U.S. Cl. .............................. 514/25; 514/26; 514/27; 424/563; 424/565

(58) Field of Search ................................ 514/25, 26, 27; 424/563, 565

(56) References Cited

U.S. PATENT DOCUMENTS

| | | | |
|---|---|---|---|
| 4,551,426 | 11/1985 | Freytag et al. ........................ | 435/7 |
| 4,665,019 | 5/1987 | Hamlyn et al. ...................... | 435/21 |
| 4,780,314 | 10/1988 | Graves ................................. | 424/95 |
| 5,164,296 | 11/1992 | Blaustein et al. ................... | 435/7.24 |
| 5,429,928 | 7/1995 | Blaustein et al. ................... | 435/7.24 |
| 5,716,937 | * 2/1998 | Haupert, Jr. ......................... | 514/25 |
| 5,891,855 | * 4/1999 | Florkiewicz ......................... | 514/26 |
| 5,910,484 | * 6/1999 | Haupert, Jr. ......................... | 514/25 |

FOREIGN PATENT DOCUMENTS

| | | |
|---|---|---|
| 0 433 074 A1 | 6/1991 | (EP) . |
| WO 92/04047 | 3/1992 | (WO) . |
| WO 97/19099 | 5/1997 | (WO) . |
| WO 98/53832 | 12/1998 | (WO) . |
| WO 00/11017 | 3/2000 | (WO) . |

OTHER PUBLICATIONS

Levenson, R., "Isoforms of the Na, K–ATPase: Family Members in Search of Function," *Rev. Physiol. Biochem. Pharmacol.*, 123:1–45 (1994).

Holzinger, et al., "Molecular basis for the insensitivity of the Monarch (Danaus plexippus) to cardiac glycosides," *FEBS* 314:477–480 (1992).

Jaisser, et al., "Primary sequence and functional expression of a novel ouabain–resistant Na, K–ATPase," *J. Biol, Chem.*, 267:16895–16903 (1992).

Sweadner, Kathleen J., "Isozymes of the $Na^+/K^+$–ATPase," *Biochem. Biophys. Acta.*, 988:185–220 (1989).

Ferrandi, M. et al., "Ouabainlike Factor in Milan Hypertensive Rats," *Am. J. Physiol.*, 263:F739–F748 (1992).

Sweadner, J., "Enzymatic propeties of separated isozymes of the Na, K–ATPase," *J. Biol. Chem.*, 260:11508–11513 (1985).

Decollogne, et al., "Biochemical characterization of the $Na^+/K^+$–ATPase isoforms in human heart," The Sodium Pump, Bamberg and Schoner (eds) pp. 812–815 (1994).

Lingrel, J.B. et al., "Na, K–ATPase: Cardiac Glycoside Binding and Functional Importance of Negatively Charged Amino Acids of Transmembrane Regions," The Sodium Pump (Bamberg and Schoner, Ed.) pp. 276–286 (1994).

Anner, B.M. et al., "Right–Side–Out Pumping Na, K–ATPase–Liposomes: A New Tool to Study the Enzyme's Receptor Function," *Biophys. Res. Commun.*, 129:102–108 (1985).

Shyjan, et al., "Antisera specific for the $\alpha 1$, $\alpha 2$, $\alpha 3$, and $\beta$ subunits of the Na, K–ATPase: Differential Expression of $\alpha$ and $\beta$ subunits in rat tissue membranes," *Biochemistry*, 28:4531–4535 (1989).

Crabos, et al., "Atrial natriuretic peptide regulates release of $Na^+$–$K^+$–ATPase inhibitor from rat brain," *Am. J. Physiol.*, 254:F912–F917 (1988).

Shull, et al., "Molecular cloning of three distinct forms of the Na+, K+–ATPase $\alpha$–subunit from rat brain," *Biochemistry*, 25:8125–8132 (1986).

Doucet, et al., "Determination of Na–K–ATPase activity in single segments of the mammalian nephron," *Am. J. Physiol.*, 237(2) :F105–F113 (1979).

De Angelis, C. et al., "Hypoxia Triggers Release of an Endogenous Inhibitor of $Na^+$–$K^+$–ATPase from Midbrain and Adrenal," *Am. J. Physiol.*, 274:F182–F188 (1988).

Haupert, G.T., "Structure and Biological Activity of the $Na^+/K^+$–ATPase Inhibitor Isolated from Bovine Hypothalamus: Difference from Ouabain," The Sodium Pump, Bamberg and Schoner (eds), Steinkopff & Darmstadt (pub), N.Y., pp. 732–742 (1994).

Sancho, J.M., "A Non–Oubain Na/K ATPhase Inhibitor Isolated from Bovine Hypothalamus. Its Relation to Hypothalamic Ouabain," *Clin. And Exper. Hypertension*, 20 (5&6), p. 535–542 (1998).

(List continued on next page.)

Primary Examiner—Frederick Krass
(74) Attorney, Agent, or Firm—Hamilton, Brook, Smith & Reynolds, P.C.

(57) ABSTRACT

The present invention is based on the unexpected discoveries that hypothalamic inhibitory factor (HIF) has a positive inotropic effect in a whole organ preparation, such as an isolated perfused heart, and that HIF, to a greater extent than ouabain, dilates the coronary arteries in the isolated perfused heart as manifested in increased coronary flow in hearts treated with HIP. The present invention relates to a method for increasing coronary perfusion in a mammalian host comprising administering to the host in need thereof an effective amount of hypothalamic inhibitory factor (HIF). The invention also relates to a method for producing an increased coronary vasodilatory effect in a mammalian host comprising administering to a mammalian host in need thereof an effective amount of HIF. The method of the present invention can be used to prevent and/or treat ischemic cardiac malfunction and coronary artery restenosis.

14 Claims, No Drawings

OTHER PUBLICATIONS

Croyle, M.L., et al., "Extensive Random Mutagenesis Analysis of the Na$^+$/K$^+$–ATPase α Subunit Identifies Known and Previously Unidentified Amino Acid Residues that Alter Ouabain Sensitivity," *Eur. J. Biochem.*, 248(2), p. 488–495 (1997).

Sergio, B. et al., "Effects of an Endogenous Ouabainlike Compound on Heart and Aorta", *Hypertension*, 17(6): Part 2:944–950 (1991).

Mathews, W.R. et al., "Mass Spectral Characterization of an Endogenous Digitalis–Like Factor From Human Plasma", *Hypertension*, 17(6): Part 2:930–935 (1991).

Ludens, J.H. et al., "Purification of an Endogenous Digitalis–like Factor From Human Plasma for Structural Analysis", *Hypertension*, 17(6): Part 2: 923–929 (1991).

Hamlyn, J.M. et al., "Identification and Characterization of a ouabain–like Compound from Human Plasma", *Proc. Natl. Acad. Sci. USA*, 88:6259–6263 (1991).

Haber, E. and Haupert, Jr., G.T., "The Search for a Hypothalamic Na, K–ATPase Inhibitors", *Hypertension*, 9:315–324 (1987).

Haupert, Jr., G.T., "Overview: Physiological Inhibitors of Na, K–ATPase Concept and Status", The Na$^+$, K$^+$–Pump Part B: Cellular Aspects, 297–320 (1988).

Mudgett–Hunter, M. et al., "High–Affinity Monoclonal Antibodies to the Cardiac Glycoside, Digoxin", *J. Immunol.*, 129(3):1165–1172 (1982).

Carilli, C.T. et al., "Hypothalamic Factor Inhibits the (Na,K) ATPase from the extracellular Surface", *J. Biol.Chem.*, 260(2):1027–1031 (1985).

Janssens, S.P. et al., "Hypothalamic Na$^+$, K$^+$–ATPase Inhibitor Constricts Pulmonary Arteries of Spontaneously Hypertensive Rats", *J. Cardio. Pharm.*, 22(*Suppl. 2*):S42–S46 (1993).

Haupert, Jr., G. T. and Sancho, J.M., "Sodium transport inhibitor from bovine hypothalamus", *Proc. Natl. Acad. Sci. USA*, 76(9):4658–4660 (1979).

Haupert, Jr., G.T. et al., "Hypothalmic sodium–transport inhibitor is a high–affinity reversible inhiitor of Na$^+$–K$^+$–ATPase", reprint from *Am. Physiol. Soc*, 247:F919–F924 (1984).

Mirsalikhova, N.M. et al., "Some Features of the Inhibition of Na$^+$, K$^+$–ATPase in Heart Muscle by Cardiotonic Glycosides", Inst. Biochem. and Inst. Chem. Plant Subst., Academy of Sciences of the Urbek SSR, Tashkent, USSR, p. 269–275, (1979).

Pitts, R.F., "Chapter 5, Clearance and Rate of Glomerular Filtration", *Physiology of the Kidney and Body Fluids* (Year Book Medical Publishers Inc., 3rd Edition, Chicago, IL) :60–63, (1981).

Mudgett–Hunter, M. et al., "Binding and Structural Diversity Among High–Affinity Monoclonal Anti–Digoxin Antibodies", *Mol. Immunol.*, 22(4) :477–488 (1985).

Smith, T. W. et al., "Treatment of Life–Threatening Digitalis Intoxication with Digoxin–Specific Fab Antibody Fragments", *The New England Journal of Medicine*, 307 (22):1357–1362 (1982).

Smith, T.W. et al., "Reversal of Advanced Digoxin Intoxication with Fab Fragments of Digoxin–Specific Antibodies", *The New England Journal of Medicine*, 294(15):797–800 (1976).

Hallaq, H.A. and Haupert, Jr., G.T., "Positive Inotropic effects of the endogenous Na$^+$/K$^+$–transporting ATPase Inhibitor form the hypothalamus,", *Proc. Natl. Acad. Sci. USA*, 86:10080–10084 (1989).

Axelrod, J., "J. Methylation reactions in the Formation and Metabolism of Catecholamines and Other Biogenic Amines", *Pharm. Rev.*, 18(1): Part I:95–113 (1966).

Thomas, R. et al., "Synthesis and Biological Activity of Semisynthetic Digitalis Analogs", *J. Pharm. Sci.*, 63(11): 1649–1683 (1974).

Hoffman, B.F. and Bigger, Jr., J.T., "Chapter 34: Digitalis and Allied Cardiac Glycosides", The Pharmacological Basics for Therapeutics, (NY: Pergamon Press):814–839 (1990).

Haupert, Jr., G.T. et al. "Target Organ Sensitivity to an Endogenous Na, K–ATpase Inhibitor from Hypothalamus", *Kidney Int.*, 31:435A (1987).

Weinberg, U. et al., "Identification and Preliminary Characterization of Two Human Digitalis–Like Substances that are Structurally Related to Digoxin and Ouabain", *Biochem. & Biophys. Res. Comm.*, 188(3):1024–1029 (1992).

Tamura, M. et al., "Isolation and Characterization of a Specific Endogenous Na$^+$, K$^+$–ATPase Inhibitor from Bovine Adrenal", *Biochem.*, 27:4244–4253 (1988).

Schoner, W. et al., "Purification and Properties of Endogenous Ouabain–like Substances from Hemofiltrate and Adrenal Glands", *J. Cardiovas. Pharm.*, 22(*Suppl.* 2):S29–S31 (1993).

Lewis, L.K. et al., "Ouabain Is Not Detectable in Human Plasma", *Hypertension*, 24(5):549–555 (1994).

Valdes, Jr., R. & Graves S.W. "Protein Binding of Endogenous Digoxin–Immunoactive Factors in Human Serum and Its Variation with Clinical Condition", *J. Clin. Endoc. Metab.*, 60(6):135–1143 (1985).

Illescas, M. et al., "Complete purification of two identical Na$^+$–pump inhibitors isolated from bovine hypothalamus and hypophysis", *FEBS Let.*, 261(2):436–440 (1990).

Zhao,N. et al., "Na,K–ATPase Inhibitors from Bovine Hypothalamus and Human Plasma Are Different from Ouabain: Nanogram Scale CD Structural Analysis", *Biochem.*, 34:9893–9896 (1995).

Tymiak et al., "Physicochemical Characterization of a Ouabain Isomer Isolated from Bovine Hypothalamus", *Proc. Natl. Acad. Sci.*, 90:8189–8193 (1993).

Nakanishi et al., "Search for an Endogenous Mammalian Cardiotonic Factor", *Saponins Used in Traditional and Modern Medicine*, pp:219–224 (1996).

Anner et al., "Hypothalamic Na$^+$–K$^+$–ATPase Inhibitors Characterized in Two–Sided Liposomes Containing Pure Renal Na$^+$–K$^+$–ATPase", *Am. J. Physiol., 258 (Renal Fluid Electrolyte Physiol., 27*):F144–F153 (1990).

Kohn, R., et al., "Endogenous Digitalis–Like Factor in Patients with Acute Myocardial Infarction," *Cor Vasa*, 34(3):227–237 1992).

Delva, P., et al., "Increase in Plasma Digitalis–Like Activity During Percutaneous Transluminal Coronary Angioplasty in Patients with Coronary Stenosis," *Life Sci.*, 47(5):385–389 (1990).

* cited by examiner

TREATMENT OF ISCHEMIC CARDIAC MALFUNCTION

RELATED APPLICATION

This application is a divisional of U.S. Ser. No. 08/866,712, filed on May 30, 1997 now U.S. Pat. No. 5,910,484, the entire teachings of which are incorporated herein by reference.

GOVERNMENT SUPPORT

The invention was supported, in whole or in part, by a grant, grant no. R01 HL 52282, from National Heart, Lung and Blood Institute. The Government has certain rights in the invention.

BACKGROUND OF THE INVENTION

While heart attack and stroke now cause fewer deaths than previously, deaths due to heart failure (inability of the heart to deliver adequate blood supply to vital organs via the systemic circulation) have increased markedly (82.5%) between 1979 and 1992. In 1997, heart failure is expected to cause at least 250, 000 deaths in the United States. More than 400, 000 new cases of heart failure are expected to be diagnosed in 1997. In all, it is estimated that more than 4 million Americans are presently living with this dangerous condition.

Sixty to seventy percent of these cases of heart failure are due to ischemic causes, i.e., insufficient delivery of blood flow and vital oxygen via the coronary circulation to the cardiac muscle. This can be due to mechanical obstruction of the coronary arteries, for example by atherosclerotic deposits, to spasm (temporary occlusion) of the coronary arteries, or to restenosis of coronary arteries that have been previously opened by angioplasty (balloon catheter dilation).

Certain segments of the general population are particularly prone to heart failure. Heart attack survivors have a four to six times greater risk of having an additional heart attack. Patients with angina (ischemic coronary pain), diabetes mellitus, or uncontrolled high blood pressure have a two-fold risk of developing heart failure compared to the general population.

Current treatments of heart failure include agents which dilate, and thus, relax blood vessels reducing arterial resistance against which the heart must work. Converting enzyme inhibitors such as captopril, enalpril and lisinopril are examples of such arterial vasodilators. Side effects such as rash, persistent cough, excessive lowering of blood pressure and adverse effects on kidney function limit the use of these agents in therapy. Other drugs which work by directly dilating blood vessels (arteries), such as hydralazine, prazocin and doxazocin also reduce the resistance against which the failing heart must pump, but these drugs too can cause excessive lowering of blood pressure, as well as reflex tachycardia (increased heart rate) which increases cardiac work and oxygen demand by the heart muscle already deprived of an adequate oxygen supply in the case of ischemic heart failure.

Because of their positive inotropic effect, cardiac glycosides (e.g., digitalis, ouabain) have been considered unrivaled in value for the treatment of heart failure. Positive inotropic effect generally refers to the enhancement of the contractility of the cardiac cells in a dose-dependent manner. Cardiac glycosides are most frequently used therapeutically to increase the adequacy of the circulation in patients with congestive heart failure and to slow the ventricular rate in the presence of atrial fibrillation.

However, cardiac glycosides have narrow therapeutic indices and their use is frequently accompanied by toxic effects that can be severe or lethal. The most important toxic effects, in terms of risk to the patient, are those that involve the heart (e.g., abnormalities of cardiac rhythm and disturbances of atrio-ventricular conduction). Gastrointestinal disorders, neurological effects, anorexia, blurred vision, nausea and vomiting are other common cardiac glycoside-induced reactions.

In the case of ischemic heart disease, other classes of compounds have been used to improve blood flow to the failing myocardium through dilation of the coronary arteries. Examples of these agents include nitrates, such as isosorbide dinitrate, and calcium channel blockers such as diltiazem, nifedipine and verapamil.

Nitrates and calcium channel blockers do not have direct effects on the contractile mechanism of the cardiac muscle cells. That is, they are not positive inotropic agents. Digitalis and ouabain, on the other hand, are strong inotropes, but do not have vasoactive (dilatory) effects on the coronary circulation. Hypothalamic inhibitory factor (HIF) has also been shown to produce a positive inotropic effect on cardiac muscle cells (U.S. patent application Ser. No. 08/338,264, filed Nov. 10, 1994 and now U.S. Pat. No. 5,716,937). However, HIF was not shown to have vasoactive (dilatory) effects on the coronary circulation.

A single compound which has both inotropic effects and coronary vasodilatory effects would be highly desirable as an agent to treat ischemic heart failure since both abnormalities are present and each contributes to the morbidity of the condition. To this point, such a compound has not been identified or made available pharmaceutically for the treatment of ischemic heart failure.

SUMMARY OF THE INVENTION

The present invention relates to a method for increasing coronary perfusion in a mammalian host comprising administering to the host in need thereof an effective amount of hypothalamic inhibitory factor (HIF). The invention also relates to a method for producing an increased coronary vasodilatory effect in a mammalian host comprising administering to a mammalian host in need thereof an effective amount of HIF.

In a particular embodiment, the invention pertains to a method for preventing or treating ischemic cardiac malfunction comprising administering to a mammalian host in need thereof an effective amount of HIF. The invention also relates to a method for preventing or treating coronary artery restenosis comprising administering to a mammalian host in need thereof an effective amount of HIF. Also encompassed by the present invention is a method for treating stenosis of a coronary artery in a mammalian host comprising administering to the host in need thereof an effective amount of HIF. Stenosis of a coronary artery can be due to, for example, atherosclerosis and/or coronary artery restenosis following the intervention of mechanical dilitation or certain bypass graft operations.

HIF slows heart rate in spontaneously beating cardiac myocytes, further reducing cardiac work and thereby diminishing oxygen requirement. The invention provides a single compound, HIF, which has the combined properties of producing a positive inotropic effect and enhancing coronary flow, and which can be used prophylactically and/or therapeutically to treat the identified conditions associated with heart failure.

DETAILED DESCRIPTION OF THE INVENTION

The present invention is based on the unexpected discoveries that hypothalamic inhibitory factor (HIF) has a positive inotropic effect in a whole organ preparation, such as an isolated perfused heart, and that HIF, to a greater extent than ouabain, dilates the coronary arteries in the isolated perfused heart as manifested in increased coronary flow in hearts treated with HIF. As defined herein "coronary flow" and/ or "coronary perfusion" refers to milliliters per minute of physiologic buffer perfusing the coronary arteries. As demonstrated herein HIF causes both enhanced contractility and simultaneous increase in coronary perfiision when administered to an intact heart. The present invention relates to methods for increasing coronary perfusion in a mammalian host comprising administering to the host in need thereof an effective amount of HIF. The present invention also relates to a method of producing a positive inotropic effect and an increased vasodilatory effect in a mammalian host comprising administering to the host in need thereof an effective amount of HIF. The mammalian host can be any mammal which is in need of increased coronary perfusion, and includes, for example, human, canine, feline, bovine and murine hosts.

HIF is an endogenous inhibitor of $Na.^+\text{-}K^+\text{-}ATPase$, which has been isolated from bovine hypothalamus and human plasma, and structurally characterized as an isomer of the plant cardiac glycoside, ouabain (Tymiak, A.A., et al., *Proc. Natl. Acad. Sci., USA*, 90:8189–8193 (1993); Zhao, N., et al., *Biochemistry*, 34:9893–9896 (1995)). HIF for use in the present invention can be obtained by purifying HIF from natural sources or chemically synthesizing HIF. In a preferred embodiment, purified HIF is used. Purified HIF refers to HIF which is substantially free of or isolated from other tissue or fluid protein components and contaminants. Various procedures may be used to purify HIF from natural sources. For example, as described in U.S. patent application Ser. No. 08/338, 264, filed Nov. 10, 1994, now U.S. Pat. No. 5,716,937 which is incorporated by reference, HIF has been purified to homogeneity using an affinity chromatography method in which purified renal $Na^+$, $K^+$-ATPase (e.g. isolated from a canine) is coupled to paramagnetic particles through a glutaraldehyde bridge (Tymiak, A.A., et aL *Proc. Natl. Acad Sci., USA*, 90:8189–8193 (1993)). The enzyme immobilizes bound HIF in the presence of $Mg^{++}$ and inorganic phosphorous with high affinity, and after washing away contaminating materials, HIF is eluted from the affinity column by chelating $Mg^{++}$ with EDTA. A subsequent IHPLC step results in purification of HIF (Tymiak, A.A., et al. *Proc. NatL. Acad. Sci., USA*, 90:8189–8193 (1993)). IF has also been purified to homogeneity using an immunoaffinity chromatography method in which an antibody which binds to HIF is coupled to the resin of an immunoaffinity column. The antibody recognizing HIF immobilizes bound HIF with high affinity, and after washing away contaminating materials, HIF is eluted from the affinity column. A subsequent HPLC step can be used to finther purify HIF. See U.S. patent application Ser. No. 08/866, 706, filed May 30, 1997, now abandoned which is incorporated by reference. It should be noted that pharmaceutically acceptable salts of HIF are also contemplated. Suitable salts include those well know to those of skill in the art.

As defined herein, an "effective amount" is an amount sufficient, when administered to the host, to result in an increased coronary vasodilatory effect and, preferably, a positive inotropic effect also in the mammalian host relative to the inotropic and coronary vasodilatory effects when an effective amount of HIF is not administered. These effects are associated with increased coronary perfusion and can be utilized to treat and/or prevent ischemic cardiac malfunction, coronary artery restenosis and stenosis of a coronary artery in a mammalian host. The amount of HIF used to treat a host will vary depending on a variety of factors, including the size, age, body weight, general health, sex and diet of the host. In addition, an effective amount of HIF will depend on the nature of the disease, and can be determined by standard clinical techniques. The precise dose to be employed will also depend on the route of administration and the seriousness of the cardiac disease or disorder, and should be decided according to the judgement of the practitioner and each patient's circumstances. However, suitable dosage ranges for intravenous administration are generally about 4.5 ug to about 20 ug per kilogram body weight. In one embodiment the dosage is about 4.5 ug per kilogram body weight, in another embodiment the dosage is about 12 ug per kilogram body weight, and in a further embodiment the dosage is about 20 ug per kilogram body weight. Suitable dose ranges for oral administration of HIF are the same as for intravenous administration of HIF, but the HIP dosage is administered orally over several days. Effective doses may be extrapolated from dose response curves derived from in vitro or animal test models.

The HIF of the present invention can be administered prophylactically to a host as a method of preventing the conditions described herein. Alternatively, HIF can be administered therapeutically to a host as a method of treating an existing disease and/or condition in the host, and can result in amelioration or elimination of the disease and/or condition.

The formulation and route of delivery of HIF to the host can be accomplished in a variety of ways. Routes of administration include intradermal, transdermal (e.g. slow release polymers), intramuscular, intraperitoneal, intravenous, intracardiac, subcutaneous, oral, epidural, and intranasal routes. Any other convenient route of administration can be used, for example, infusion or bolus injection, or absorption through epithelial or mucocutaneous linings. The HIF can be administered together with other components or biologically active agents, such as pharmaceutically acceptable surfactants (e.g., glycerides), carriers (e.g., saline, buffered saline, dextrose, water, glycerol, ethanol), excipients (e.g., lactose), diluents and vehicles and combinations thereof. The formulation should suit the mode of administration.

The composition can also include, if desired, minor amounts of wetting or emulsifing agents, or pH buffering agents. The composition can be a liquid solution, suspension, emulsion, tablet, pill, capsule, sustained release formulation or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the HIF is formulated in accordance with routine procedures as a pharmaceutical composition adapted for intravenous administration to the mammalian host (e.g., a human). For example, HIF for intravenous administration can be a solution in sterile isotonic aqueous buffer. Where necessary, the HIF composition may also include a solubilizing agent and a local anesthetic to ease pain at the site of injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is administered by injection, an ampule of sterile water for injection or saline can be provided so that the ingredients may be mixed prior to administration. Thus, the invention also relates to the use of HIF in the manufacture of medicaments for the treatment and/or prevention of ischemic cardiac malfunction, coronary artery restenosis and/or stenosis of a coronary artery.

The invention can be used to prevent and/or treat a patient with ischemic heart failure, which is due, for example, to stenosis of the coronary artery. It is estimated that four million Americans suffer from heart failure, and that 60–70% of these cases (2.4–2.8 million) are on the basis of ischemic disease. The combined advantages over digitalis and ouabain of less toxicity and enhanced coronary perfusion makes the invention a therapeutically desirable substitute for digitalis in these patients.

The invention also relates to methods wherein HIF is administered to prevent and/or treat coronary artery restenosis in patients who have undergone coronary artery angioplasty or certain kinds of coronary artery bypass surgery for conditions such as ischemic heart disease.

HIF does not manifest the same toxicity profile as the cardiac glycosides. Therefore, prevention and/or treatment of conditions associated with heart failure, such as ischemic cardiac failure and coronary artery restenosis, with HIF can be accomplished with less risk of toxicity to the patient, and both abnormal muscular contractility and inadequate flow of blood and oxygen to the ischemic myocardium can be concurrently treated and/or prevented with a single compound.

This invention is illustrated further by the following exemplification, which is not to be construed as limiting in any way.

EXEMPLIFICATION

Measurement of Positive Inotropic Effects and Coronary Flow

Guinea pigs were anesthetized with 65–100 mg pentobarbital in the peritoneal cavity followed by anticoagulation using 200 units of heparin via femoral vein. Sternotomy was performed, the beating heart removed and placed in a bowl containing room temperature saline. The aorta was trimmed and cannulated onto the perfusion apparatus. Retrograde perfusion of Kreb's solution (37° C.) at 70 mm Hg bubbled with 95% $O_2$/5% $CO_2$ from a 3 liter reservoir was begun within one minute of cardiectomy. A micro flexible temperature probe was inserted in the open pulmonary artery allowing coronary effluent to drain. The left atrial appendage was incised, the left ventricle vented, and a water-filled balloon-tipped catheter inserted into the left ventricle chamber. Left ventricular systolic pressure (LVP), left ventricular end diastolic pressure (LVEDP), maximal rate of rise of left ventricular pressure (dP/dT), and aortic root pressure (AOP) were recorded on a precalibrated multichannel dynograph. Coronary flow (CF) is measured by timed volumetric collection. The heart was paced (HR) at 272 BPM by way of electrodes attached to the right atrium. After 30 minutes of perfusion, coronary flow was then diverted into a recirculating perfusion circuit primed with 60 cc of Kreb's solution.

The circuit was started with the coronary effluent draining into a reservoir. The effluent was pumped out the reservoir through a 5 micron filter that passed through a low volume silastic oxygenator and up a pressure column. The oxygenated effluent flowed back to the aorta or out an overflow column that drained to the reservoir. Pump output was kept higher that the coronary flow allowing a constant aortic root pressure. Heart temperature (HT), pH, $O_2$ and $CO_2$ of the perfusate were held constant by water jacketing the oxygenator and perfusion circuit and no additional Kreb's solution needed to be added during the recirculation intervals. During the first ten minutes of recirculating, the intraventricular balloon volume was adjusted to reach an LVEDP of 10 mm Hg. The heart was switched back to non-recirculation for ten minutes while the recirculating circuit was emptied and refilled with fresh Kreb's solution. Two additional recirculation non-recirculation cycles were carried out with LVEDP adjusted and parameters measured. LVP, LVEDP, dP/dT, AOP, HR, HT and CF were recorded at 5 minute intervals for 15 minutes. Then a coded aliquot of ouabain, HIF or placebo was added to the recirculating Kreb's solution. Parameters continued to be measured at 5 minute intervals for 30 additional minutes. Results HIF has been previously shown to produce positive inotropic effects in isolated, spontaneously beating myocytes in culture, with greater potency and a different toxic profile from ouabain (Hallaq, H. and Haupert, G., Jr., *Proc. Natl. Acad Sci, USA*, 86:10080–10084 (1989)). As shown herein, HIF also produces a positive inotropic effect in an intact, whole organ preparation. 20 µg HIF was prepared to homogeneity as confirmed by mass spectral measurement, for infusion into an isolated, perfused guinea pig heart preparation according to the Langendorf methodology (Hendren, W.G., et al., *J. Thor. Cardiovasc. Surg.*, 94:614–625 (1987)). This methodology allows continuous measurement of left ventricular pressure generation, the first derivative of the pressure measurement (dP/dT), end diastolic pressure and coronary flow. Pilot studies with ouabain were carried out to determine the minimal consistently effective dose to produce an enhanced inotropic effect. For both ouabain and HIF, this amount was 4 µg of pure inhibitor administered to a perfusion volume of 60 ml Krebs-Heinsleit buffer (final concentration $1 \times 10^{-7}$ M). Coded samples were prepared of HIF, ouabain and placebo (vehicle), and administered randomly to the preparation. The one conducting the experiments was blinded to the samples.

Results are shown in the Table. The Table shows the effects of HIF, ouabain and placebo on performance characteristics and coronary flow in isolated, perfused guinea pig heart. Both HIF and ouabain showed significant increases in left ventricular pressure (lvp) and rate of development of pressure (dP/dT) compared to the preadministration control period, indicating positive inotropic response. Placebo produced no change. HIF and ouabain also produced a statistically significant increase in coronary flow, but the percent increase from baseline for HIF surprisingly was two-fold greater than the increase produced by ouabain (Table). Thus, the mammalian-derived HIF was a significantly more potent coronary vasodilator than the plant-derived ouabain. HIF produced a statistically significant increase in coronary flow and is less toxic than ouabain.

TABLE 1

Effects of HIF, ouabain and placebo on performance and perfusion characteristics in isolated, perfused guinea pig heart (LVP, left ventricular pressure; dP/dt, rate of development of pressure)

| GROUPS | LVP | LVP post intervention | % | dPdt mmHg · sec − 1 | dP/dt post intervention | % | End Dia pressure | EDP post intervention | % | coronary flow cc/min | CF post intervention | % |
|---|---|---|---|---|---|---|---|---|---|---|---|---|
| ouabain n = 9 | 73.82 | 90.44^* | 22.5 | 2326 | 2856^* | 22.7 | 7.66 | 8.01 | 4.6 | 25.84 | 27.77* | 7.5 |
| placebo n = 8 | 67.17 | 68.29 | 1.7 | 2104 | 2088 | −0.7 | 7.77 | 9.19 | 18.2 | 25.89 | 25.09 | −3.1 |
| HIF n = 9 | 70.54 | 89.91^* | 27.4 | 2292 | 2884^* | 25.8 | 7.6 | 7.77 | 2.1 | 24.37 | 27.82* | 14.1 |

^P < 0.01 intervention vs placebo
*P < 0.01 pre intervention vs post intervention

EQUIVALENTS

Those skilled in the art will recognize, or be able to ascertain using no more than routine experimentation, numerous equivalents to the specific embodiments of the invention described herein. Such equivalents are intended to be encompassed in the scope of the following claims.

I claim:

1. A method for producing an increased coronary vasodilatory effect in a mammalian host comprising administering to a mammalian host in need thereof an effective amount of a glycosidic hypothalamic inhibitory factor, wherein said factor has been purified to homogeneity.

2. The method of claim 1 wherein the mammalian host is a human.

3. The method of claim 1 wherein the hypothalamic inhibitory factor is administered intravenously.

4. A method for preventing or treating ischemic cardiac malfunction comprising administering to a mammalian host in need thereof an effective amount of a glycosidic hypothalamic inhibitory factor, wherein said factor has been purified to homogeneity.

5. The method of claim 4 wherein the mammalian host is a human.

6. The method of claim 4 wherein the ischemic cardiac malfunction is due to stenosis of the coronary artery.

7. The method of claim 4 wherein the hypothalamic inhibitory factor is administered intravenously.

8. A method for preventing or treating coronary artery restenosis comprising administering to a mammalian host in need thereof an effective amount of a glycosidic hypothalamic inhibitory factor, wherein said factor has been purified to homogeneity.

9. The method of claim 8 wherein the mammalian host is a human.

10. The method of claim 8 wherein the hypothalamic inhibitory factor is administered intravenously.

11. A method for treating stenosis of a coronary artery in a mammalian host comprising administering to a host in need thereof an effective amount of a glycosidic hypothalamic inhibitory factor, wherein said factor has been purified to homogeneity.

12. The method of claim 11 wherein stenosis of the coronary artery is due to coronary artery restenosis.

13. The method of claim 11 herein the mammalian host is a human.

14. The method of claim 11 wherein the hypothalamic inhibitory factor is administered intravenously.

* * * * *